US006998105B2

(12) United States Patent
Ruys et al.

(10) Patent No.: US 6,998,105 B2
(45) Date of Patent: Feb. 14, 2006

(54) LOW DENSITY RADIONUCLIDE-CONTAINING PARTICULATE MATERIAL

(75) Inventors: Andrew John Ruys, Pymble (AU); Bruce Nathaniel Gray, Claremont (AU)

(73) Assignee: Sirtex Medical Limited, New South Wales (AU)

(*) Notice: Subject to any disclaimer, the term of this patent is extended or adjusted under 35 U.S.C. 154(b) by 174 days.

(21) Appl. No.: 10/173,497

(22) Filed: Jun. 17, 2002

(65) Prior Publication Data

US 2002/0197208 A1 Dec. 26, 2002

Related U.S. Application Data

(63) Continuation of application No. PCT/AU01/01369, filed on Oct. 25, 2001.

(30) Foreign Application Priority Data

Oct. 25, 2000 (AU) .................................. PR0982

(51) Int. Cl.
*A61K 51/00* (2006.01)
(52) U.S. Cl. .................. 424/1.37; 424/1.11; 424/1.29; 424/1.33; 424/1.65
(58) Field of Classification Search ............... 424/1.11, 424/1.29, 1.33, 1.37, 1.65, 9.3, 9.4, 9.5, 400, 424/450; 128/662.02, 660.01, 653.1

See application file for complete search history.

(56) References Cited

U.S. PATENT DOCUMENTS

| 4,889,707 | A   |   | 12/1989 | Day et al. |           |
|-----------|-----|---|---------|------------|-----------|
| 5,362,473 | A   |   | 11/1994 | Panek      |           |
| 5,885,547 | A   | * | 3/1999  | Gray       | 424/1.37  |
| 6,149,889 | A   |   | 11/2000 | Chin et al.|           |
| 6,258,338 | B1  | * | 7/2001  | Gray       | 424/1.29  |
| 6,537,518 | B1  | * | 3/2003  | Gray       | 424/1.29  |
| 2002/0197207 | A1 | * | 12/2002 | Ruys et al. | 424/1.11 |
| 2003/0203205 | A1 | * | 10/2003 | Bi et al.  | 428/402   |

FOREIGN PATENT DOCUMENTS

| WO | 8603124 | 6/1986 |
|----|---------|--------|
| WO | 9519841 | 7/1995 |
| WO | 0045826 | 8/2000 |

OTHER PUBLICATIONS

Shepherd, F. et al., *Cancer*, vol. 70, No. 9, pp. 2250-2254 (Nov. 1, 1992).
Burton, M.A. et al., *Europ. J. Cancer Clin. Oncol.*, 25:1487-1491 (1989).
Burton, M.A. et al., *Europ. J. Cancer Clin. Oncol.*, 24(8): 1373-1376 (1988).
Meade, V. et al., *Europ. J. Cancer Clin. Oncol.*, 23:37-41 (1987).

* cited by examiner

*Primary Examiner*—Dameron L. Jones
(74) *Attorney, Agent, or Firm*—Merchant & Gould PC

(57) ABSTRACT

The invention relates to a particulate material consisting of a low density radiation-tolerant glass and a radionuclide incorporated into the low density glass or coated on the low density glass, the glass having a density of less than 2.5 g/cm$^3$, processes for its production and a method of radiation therapy utilising the patentable material.

20 Claims, No Drawings

LOW DENSITY RADIONUCLIDE-CONTAINING PARTICULATE MATERIAL

This application is a continuation of PCT/AU01/01369, filed Oct. 25, 2001.

FIELD OF THE INVENTION

This invention relates to a particulate material comprising a low density inorganic glass material containing a radionuclide either within the matrix of the material or coated onto the surface, to a method for the production thereof, and to methods for the use of this particulate material.

In one particular aspect, this invention relates to a low-density inorganic glass microspheres that are loaded with or coated with a radionuclide such as radioactive yttrium, and to the use of these low-density radionuclide-containing microspheres in the treatment of cancer in humans and other mammals. In this aspect, the low-density inorganic microspheres of the invention are designed to be administered into the arterial blood supply an organ to be treated, whereby they become entrapped in the small blood vessels of the target organ and irradiate it. The low density is necessary in order for the microspheres to be able to be transported into the target organ by blood flow.

The particulate material of the present invention therefore has utility in the treatment of various forms of cancer and tumours, but particularly in the treatment of primary and secondary cancer of the liver and the brain. It is to be understood that the particulate material of the invention is not limited to radioactive microspheres, but may be extended to other radioactive particles which are suitable for use in the treatment methods described herein.

BACKGROUND OF THE INVENTION.

Many previous attempts have been made to locally administer radioactive materials to patients with cancer, as a form of therapy. In some of these, the radioactive materials have been incorporated into small particles, seeds, wires and similar related configurations that can be directly implanted into the cancer. When radioactive particles are administered into the blood supply of the target organ, the technique has become known as Selective Internal Radiation Therapy (SIRT). Generally, the main form of application of SIRT has been its use to treat cancers in the liver.

There are many potential advantages of SIRT over conventional, external beam radiotherapy. Firstly, the radiation is delivered preferentially to the cancer within the target organ. Secondly, the radiation is slowly and continually delivered as the radionuclide decays. Thirdly, by manipulating the arterial blood supply with vasoactive substances (such as Angiotensin-2), it is possible to enhance the percentage of radioactive particles that go to the cancerous part of the organ, as opposed to the healthy normal tissues. This has the effect of preferentially increasing the radiation dose to the cancer while maintaining the radiation dose to the normal tissues at a lower level (Burton, M. A. et al.; Effect of Angiotensin-2 on blood flow in the transplanted sheep squamous cell carcinoma. *Europ. J Cancer Clin. Oncol.* 1988, 24(8):1373–1376).

When microspheres or other small particles are administered into the arterial blood supply of a target organ, it is desirable to have them of a size, shape and density that result in the optimal homogeneous distribution within the target organ. If the microspheres or small particles do not distribute evenly, and as a function of the absolute arterial blood flow, then they may accumulate in excessive numbers in some areas and cause focal areas of excessive radiation. It has been shown that microspheres of approximately 25–50 micron in diameter have the best distribution characteristics when administered into the arterial circulation of the liver (Meade, V. et al.; Distribution of different sized microspheres in experimental hepatic tumours. *Europ. J. Cancer & Clin. Oncol.* 1987, 23:23–41).

If the microspheres or small particles do not contain sufficient ionising radiation, then an excessive number will be required to deliver the required radiation dose to the target organ. It has been shown that if large numbers of microspheres are administered into the arterial supply of the liver, then they accumulate in and block the small arteries leading to the tumour, rather than distribute evenly in the capillaries and precapillary arterioles of the tumour.

Therefore, it is desirable to use the minimum number of microspheres that will provide an even distribution in the vascular network of the tumour circulation.

If the microspheres or small particles are too dense or heavy, then they will not distribute evenly in the target organ and will accumulate in excessive concentrations in parts of the liver that do not contain the cancer. Heavy microspheres, particularly microspheres with a density greater than about 2.3, can be difficult to deliver through infusion tubing as they settle within the tubing unless the injection force is great and the flow rate of the suspending fluid is high. High pressures and fast delivery flow rates are absolutely contra-indicated when infusing radioactive microspheres into the hepatic artery of patients as the microspheres will reflux back into inappropriate blood vessels such as the gastro-duodenal artery, splenic artery and left gastric artery. This will result in severe and even fatal consequences.

In addition, high density microspheres do not distribute evenly within the target organ and settle heterogeneously within the tissues. This, in turn, decreases the effective radiation reaching the cancer in the target organ, which decreases the ability of the radioactive microspheres to kill the tumour cells. In contrast, lighter microspheres distribute well within the liver (Burton, M. A. et al.; Selective International Radiation Therapy; Distribution of radiation in the liver. *Europ. J. Cancer Clin. Oncol.* 1989, 25:1487–1491).

In the earliest clinical use of yttrium-90-containing microspheres, the yttrium was incorporated into a polymeric matrix that was formulated into microspheres. While these microspheres were of an appropriate density to ensure good distribution characteristics in the liver, there were several instances in which the yttrium-90 leached from the microspheres and caused inappropriate radiation of other tissues.

In one attempt to overcome the problem of leaching, a radioactive microsphere comprising a biologically compatible glass material containing a beta- or gamma-radiation emitting radioisotope such as yttrium-90 distributed homogeneously throughout the glass as one of the glass component oxides, has been developed (International Patent Publication No. WO 86/03124). These microspheres are solid high density glass and contain the element yttrium-89 as a component of the glass, which can be activated to the radionuclide yttrium-90 by placing the microspheres in a neutron beam. These glass microspheres have several disadvantages including being of a higher density than is desirable, i.e., more than 2.5 g/cm$^3$, and containing significant amounts of other elements such as glass modifier oxides and fluxing oxides which are activated to undesirable radionuclides when placed in a neutron beam. This is as result of the glass composition used to produce the microspheres. It has also been shown in clinical studies of patients that pre-treatment imaging with technetium-99 labelled microspheres cannot be used to predict the behaviour of these solid glass microspheres. As pre-treatment imaging and dosimetry is very commonly used when treating patients with SIRT, this is a distinct disadvantage of the solid glass microspheres described in International Patent Publication No. WO 86/03124. These glass microspheres have also been shown to lodge in inappropriate tissues.

There have been several reports of clinical studies on the use of solid glass radioactive microspheres. In one report, ten patients with primary hepatocellular carcinoma were treated, however no patient had a complete or partial response (Shepherd, F. et al., Cancer, Nov. 1, 1992, Vol.70, No.9, pp 2250–2254).

Another approach has been focussed on the use of small hollow or cup-shaped ceramic particles or microspheres, wherein the ceramic base material consists or comprises yttria or the like (see International Patent Application No. PCT/AU95/00027; WO 95/19841). These microspheres were developed to overcome the high density problem associated with the solid glass microspheres.

For radioactive microspheres to be used successfully for the treatment of cancer, the radiation emitted from the microspheres should be of high energy and short range. This ensures that the energy emitted from the microspheres will be deposited into the tissues immediately around the microspheres and not into tissues which are not the target of the radiation treatment. There are many radionuclides that can be incorporated into microspheres that can be used for SIRT. Of particular suitability for use in this form of treatment is the unstable isotopes of yttrium (Yttrium-90). Yttrium-90 is the unstable isotope of yttrium-89 that can be manufactured by placing the stable yttrium-89 in a neutron beam. The yttrium-90 that is generated decays with a half life of 64 hours, while emitting a high energy pure beta radiation. Other candidate radionuclides for this invention include but are not restricted to holmium, iodine, phosphorous, iridium, rhenium, and samarium.

If the microspheres contain other radioactive substances that are not required for the radiation treatment of the target tissue, then unwanted and deleterious radiation effects may occur. It is therefore desirable to have microspheres of such a composition that they only emit radiation of the desired type to achieve the therapeutic effect. In this treatment mode, it is desirable to have microspheres that emit high energy but short penetration beta-radiation that will confine the radiation effects to the immediate vicinity of the microspheres.

SUMMARY OF THE INVENTION

In one aspect, the present invention provides a particulate material comprising a low density radiation-tolerant glass and a radionuclide incorporated into the low density glass or coated on the low density glass, the glass having a density of less than 2.5 g/cm$^3$.

Preferably, the low density glass comprises $SiO_2$ and $B_2O_3$ and the weight percentage of [$SiO_2+B_2O_3$] in the glass is at least 70%, more preferably at least 80%, 85% or even 90%. Preferably, the $SiO_2$ content of the glass is at least 60% by weight, and the $B_2O_3$ content is at least 10% by weight.

The present invention also provides a method of radiation therapy of a patient which comprises administration to the patient of a particulate material as discussed above.

The present invention also provides for the use of a particulate material as discussed above in radiation therapy of a patient.

In another aspect, the present invention provides a process for the production of a particulate material as described above comprising melting together a low density radiation-tolerant glass and a radionuclide and solidifying the melt to produce a particulate material. Alternatively, the melt may include a radionuclide precursor which is subsequently activated to form the radionuclide.

Alternatively, the present invention provides a process comprising the steps of forming a low density radiation-tolerant glass core and coating the core with a radionuclide. Alternatively, the core may be coated with a radionuclide precursor which is subsequently activated to form the radionuclide.

DETAILED DESCRIPTION OF THE INVENTION

The particulate material of this invention is a low density material having a density of less than 2.5 g/cm$^3$. Preferably the material has a density of less than 2.4, more preferably less than 2.3 or even 2.2 g/cm$^3$. Such low density material contains little or none of the fluxing oxides and modifier oxides that may be activated to undesirable radionuclides when placed in a neutron beam.

Preferably, the particulate material comprises microspheres having a diameter in the range of from 5 to 200 microns, more particularly 15 to 100 microns. Particularly preferred are microspheres in the range of 20 to 50 microns, especially from 30 to 35 microns.

As previously described, the low density glass preferably comprises $SiO_2$ and $B_2O_3$, with the weight percentage of [$SiO_2+B_2O_3$] in the glass being at least 70%, preferably at least 80% or even at least 90%. Suitable low density glasses are set out by way of example in the following Table:

| Composition | Density | $SiO_2$ | $Al_2O_3$ | $B_2O_3$ | $Li_2O$ | $Na_2O$ | $K_2O$ | $Y_2O_3$ |
|---|---|---|---|---|---|---|---|---|
| 1 | 2.27 | 75 | 2 | 15 | | 4 | 2 | 2 |
| 2 | 2.24 | 66 | 3 | 22 | | 4 | 3 | 2 |
| 3 | 2.24 | 67 | 2 | 23 | | 6 | | 2 |
| 4 | 2.29 | 66 | 3 | 18 | 1 | 1 | 9 | 2 |
| 5 | 2.13 | 71 | 1 | 24 | .5 | .5 | 1 | 2 |
| 6 | 2.26 | 80 | 2 | 12 | | 4 | | 2 |
| 7 | 2.23 | 79 | 2 | 13 | | 4 | | 2 |
| 8 | 2.24 | 77 | 2 | 15 | | 3 | 1 | 2 |
| 9 | 2.24 | 64 | 5 | 22 | | 7 | | 2 |
| 10 | 2.16 | 64 | 5 | 26 | 1 | 2 | | 2 |
| 11 | 2.23 | 79 | 2 | 13 | | 4 | | 2 |

In each case, the formulation is in weight percent oxide.

One particularly preferred low density glass composition is a composition containing 72% $SiO_2$, 25% $B_2O_3$, 1% $Al_2O_3$, 0.5% $Li_2O$, 0.5% $Na_2O$ and 1% $K_2O$, which has a true density of 2.13 g/cm$^3$.

Yttria is a dense ceramic (5.0 g/cm$^3$), however yttria can be successfully incorporated into the glass composition in small amounts, either into the matrix of the glass or as a surface coating, while maintaining the density of the particulate material less than 2.5 g/cm$^3$.

In a further embodiment of this invention, the low density glass may comprise from 95% to 100% $SiO_2$. In this instance, the radionuclide is incorporated onto the microsphere as a surface coating, rather than being incorporated into the matrix of the glass.

The radionuclide which is incorporated into particulate material in accordance with the present invention is preferably yttrium-90.

If the particulate material contains other radioactive substances that are not required for the radiation treatment of the target tissue, then unwanted and deleterious radiation effects may occur. It is therefore preferably to have the particulate material of such a composition that it contains a single desired radionuclide. In a treatment mode, it is preferably emit high energy but short penetration beta-radiation which will confine the radiation effects to the immediate vicinity. For this purpose, yttrium-90 is a preferred radionuclide. Yttrium-90 has a half life of 64 hours and emits β radiation. However, other radionuclides may also be used in place of yttrium-90 of which the isotopes of holmium, samarium, iodine, iridium, phosphorus, rhenium are some examples.

In some situations, it may be desirable to incorporate a second radionuclide, for example one that will have a specific gamma emission so that the gamma emission can be used for either dosimetry or imaging using a gamma camera. Such a gamma emission will be in addition to the emission of the primary therapeutic radionuclide in the particulate material of this invention.

Preferably, the particulate material of this invention is in the form of low density glass microspheres. The radionuclide (or radionuclide precursor such as yttrium-89) can be incorporated into the low density glass by mixing powdered yttria to the powdered base materials of the glass and melting all the components together to form a liquid composite material that is cooled to form a solid. The solid composite material is then crushed to the desired size and the frit suitably heated to spheroidise the particles. The particles are then sized to collect the microspheres with the desired size range. By limiting the amount of yttria or other radionuclide that is added to the base material or is applied as a coating, the final microsphere density can be limited to less than 2.5, 2.4, 2.3 or 2.2.

As an alternative to incorporating the yttria or other radionuclide into the matrix of the microspheres, the radionuclide (or radionuclide precursor) can be coated onto the surface of the microsphere matrix by a number of means including:

(i) the radionuclide may be deposited onto the microsphere cores using finely-divided solid radionuclide material, such as a yttria colloidal sol. Adhesion in this case will be via electrostatic forces such as heterocoagulation, followed by permanent fixation by solid state diffusion via heat-treatment methods; or (ii) the radionuclide may be deposited onto the microsphere cores using a gas-entrained radionuclide precursor, for example an aerosol utilising an electrostatic attachment mechanism, or a radionuclide precursor vapour such as a sputter-coating process, chemical vapour deposition process, or physical vapour deposition process; or (iii) the radionuclide may be deposited onto the glass microspheres using a radionuclide precursor solution, for example a solution of radionuclide salt, or a solution of radionuclide alkoxide or other radionuclide organometallic. Adhesion in this case would be via precipitation of an insoluble film that may or may not be subjected to a post-coating heat-treatment procedure for the purposes of enhancing fixation.

Preferably, the radionuclide is stably incorporated onto non-porous low-density glass microspheres by precipitating it from a chemical solution of radionuclide precursor, however the present invention also extends to coating from a vapour or solid radionuclide source.

As used herein, references to the radionuclide being stably incorporated into the glass microspheres are to be understood as referring to incorporation of the radionuclide so that it does not leach out of, or spall from, the microspheres under physiological conditions, such as in the patient or in storage.

Where a radionuclide precursor such as yttrium-89 is either incorporated into low density glass or is coated on the surface of glass microspheres, it is then made radioactive by neutron-irradiation or other technique.

Since the radionuclide is stably incorporated into or onto the microspheres, the present invention provides microspheres with improved characteristics arising from the fact that they can be formulated to be of such a size, shape and density that they have improved distribution characteristics when administered into the arterial supply of target organs to be treated. Preferably, the microspheres are formulated in substantially spherical form and have a preferred diameter in the range of from 15 to 100 microns, preferably from 20–50 micron and more preferably from 30 to 35 microns. The size of the microspheres should be as uniform as possible to achieve best results in subsequent use. The microspheres are also formulated to have a specific gravity of less than 2.5 so as to assist in even distribution of the microspheres within the target organ, particularly within the liver.

The present invention also provides a method of radiation therapy of a human or other mammalian patient, which comprises administration to the patient of a particulate material as described above.

In yet another aspect, this invention also extends to the use of a particulate material as described above in radiation therapy of a human or other mammalian patient.

Throughout this specification, unless the context requires otherwise, the word "comprise", and or variations such as "comprises" or "comprising", will be understood to imply the inclusion of a stated integer or step or group of integers or steps but not the exclusion of any other integer or step or group of integers or steps.

Further features of the present invention are more fully described in the following Examples. It is to be understood, however, that this detailed description is included solely for the purposes of exemplifying the present invention, and should not be understood in any way as a restriction on the broad description of the invention as set out above.

EXAMPLE 1

High-purity oxide components are batched in accordance with the following glass composition given in percentages by weight: 72% $SiO_2$, 25% $B_2O_3$, 1% $Al_2O_3$, 0.5% $Li_2O$, 0.5% $Na_2O$, 1% $K_2O$, a glass composition which has a specific gravity of 2.13. To this is added the required amount of yttria or other required radionuclides and the mixture of parent oxides is smelted in a contamination-free crucible, homogenised, and then quenched in demineralised water to produce the frit. The frit is then ground and sieved to yield a 20 to 50 micron size range fraction. This sieved frit is then flame spheroidised by passing the powder from a feed hopper through a flame torch. The resultant product is sieved into the 30 to 35 micron size range fraction.

If the microspheres are to be surface coated with a radionuclide such as yttria instead of incorporating it into the matrix of the microsphere, then the exact same steps are taken with the exception that the radionuclide is not added to the components that form the matrix. In this case a one wt % suspension of the microspheres in alcohol is prepared and placed in a beaker on a magnetic stirrer inside a glove box. Yttrium alkoxide or other material that will produce the required radionuclide is added at an amount necessary to produce a surface coating, eg., an amount such that the yttria yield from the yttrium alkoxide is 2.4 wt % of the weight of microspheres. After a period of mixing, the yttrium alkoxide is hydrolysed. The microspheres are then rinsed with three repeats, and then dried.

The coated microspheres are then irradiated in a neutron beam, sterilised, and packed in a sterile tube.

EXAMPLE 2

The technique of Selective Internal Radiation Therapy (SIRT) has been described above. It involves either a laparotomy to expose the hepatic arterial circulation or the insertion of a catheter into the hepatic artery via the femoral, brachial or other suitable artery. This may be followed by the infusion of Angiotensin-2 into the hepatic artery to redirect arterial blood to flow into the metastatic tumour component of the liver and away from the normal parenchyma. This is followed by embolisation of yttrium-90 coated microspheres (produced in accordance with Example 1) into the arterial circulation so that they become lodged in the microcirculation of the tumour. Repeated injections of microspheres are made until the desired radiation level in the normal liver parenchyma is reached. By way of example, an amount of yttrium-90 activity that will result in an inferred radiation dose to the normal liver of approximately 80 Gy may be delivered. Because the radiation from SIRT is delivered as a series of discrete point sources, the dose of 80 Gy is an average dose with many normal liver parenchymal cells receiving much less than that dose.

The measurement of tumour response by objective parameters including reduction in tumour volume and serial estimations of serum carcino-embryonic antigen (CEA) levels is an acceptable index of the ability of the treatment to alter the biological behaviour of the tumour.

The invention claimed is:

1. A particulate material comprising a low density radiation-tolerant glass and one or two radionuclides incorporated into the low density glass, the glass having a density of less than 2.5 g/cm$^3$, wherein the radionuclide is an isotope selected from the group consisting of holmium, samarium, iodine, iridium, rhenium, and yttrium, and wherein the low density glass comprises $SiO_2$ and $B_2O_3$, and the weight percentage of [$SiO_2+B_2O_3$] in the glass is at least 70%.

2. The particulate material according to claim 1, wherein the density of the glass is less than 2.4 g/cm$^3$.

3. The particulate material according to claim 1, wherein low density glass comprises from 95% to 100% $SiO_2$.

4. The particulate material according to claim 1, wherein the weight percentage of [$SiO_2+B_2O_3$] in the glass is at least 80%.

5. The particulate material according to claim 1, wherein the $SiO_2$ content of the glass is at least 60% by weight, and the $B_2O_3$ content is at least 10% by weight.

6. The particulate material according to claim 1, wherein the composition of the glass is 72% $SiO_2$, 25% $B_2O_3$, 1% $Al_2O_3$, 0.5% $Li_2O$ 0.5% $Na_2O$ and 1% $K_2O$.

7. The particulate material according to claim 1, which is a microsphere having a diameter in the range of from 5 to 200 microns.

8. The particulate material according to claim 7, wherein the diameter is in the range of from 15 to 100 microns.

9. The particulate material according to claim 1, wherein the radionuclide is yttrium-90.

10. A process for the production of a particulate material according to claim 1 comprising melting together a low density radiation-tolerant glass and a radionuclide or radionuclide precursor and solidifying the melt to produce a particulate material, and then if necessary activating the precursor to form the radionuclide.

11. The process according to claim 10, wherein the radionuclide is yttrium-90.

12. A method of radiation therapy of a patient, which comprises administration to the patient of a particulate material according to claim 1.

13. The method according to claim 12, wherein the radionuclide is yttrium-90.

14. The method according to claim 12, wherein the radiation therapy comprises treatment of a primary or secondary liver cancer.

15. The particulate material according to claim 1, wherein the density of the glass is less than 2.3 g/cm$^3$.

16. The particulate material according to claim 1, wherein the density of the glass is less than 2.2 g/cm$^3$.

17. The particulate material according to claim 1, wherein the weight percentage of [$SiO_2+B2O_3$] in the glass is at least 85%.

18. The particulate material according to claim 1, wherein the weight percentage of [$SiO_2+B2O_3$] in the glass is at least 90%.

19. The particulate material according to claim 7, wherein the diameter is in the range of from 20 to 50 microns.

20. The particulate material according to claim 7, wherein the diameter is in the range of from 30 to 35 microns.

* * * * *